United States Patent
Banaszak et al.

(10) Patent No.: US 6,575,620 B1
(45) Date of Patent: Jun. 10, 2003

(54) METHOD AND DEVICE FOR VISUALLY MEASURING STRUCTURAL FATIGUE USING A TEMPERATURE SENSITIVE COATING

(75) Inventors: David Banaszak, New Carlisle, OH (US); Gary Dale, Kettering, OH (US); Jeffrey D. Jordan, Hampton, VA (US); A. Neal Watkins, Hampton, VA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/504,428

(22) Filed: Feb. 15, 2000

(51) Int. Cl.⁷ .............................. B06B 3/00; G01N 25/72
(52) U.S. Cl. ................................ 374/4; 73/663; 73/577
(58) Field of Search .................... 374/4–7, 4.5, 46, 374/57, 117, 192, 52, 118; 73/662, 663, 668, 665, 802, 583, 577, 808

(56) References Cited

U.S. PATENT DOCUMENTS

| | | | |
|---|---|---|---|
| 3,808,439 A | * | 4/1974 | Renius ........................ 250/334 |
| 4,034,264 A | | 7/1977 | Muller et al. .................... 361/2 |
| 4,075,493 A | * | 2/1978 | Wickersheim .......... 250/461 R |
| 4,408,881 A | * | 10/1983 | Clarady, Jr. et al. ........ 356/347 |
| 4,489,612 A | * | 12/1984 | Griggs ......................... 73/663 |
| 4,783,999 A | * | 11/1988 | Kimball ........................ 73/665 |
| 4,826,326 A | * | 5/1989 | Reynolds et al. ............... 374/5 |
| 4,885,633 A | * | 12/1989 | Buck ........................... 358/93 |
| 4,895,156 A | * | 1/1990 | Schulze ....................... 128/634 |
| 5,015,950 A | * | 5/1991 | Rose et al. ................... 324/224 |
| 5,085,073 A | * | 2/1992 | Heyman et al. ............... 73/147 |
| 5,111,048 A | * | 5/1992 | Devitt et al. ................. 250/342 |
| 5,146,289 A | * | 9/1992 | Newman .................... 356/355 |
| 5,201,841 A | * | 4/1993 | Lebeau et al. .................. 374/5 |
| 5,208,528 A | * | 5/1993 | Quintard ................. 324/158 R |
| 5,341,676 A | * | 8/1994 | Gouterman et al. .......... 73/147 |
| 5,453,615 A | * | 9/1995 | Mis ............................. 250/303 |
| 5,525,796 A | | 6/1996 | Haake .................... 250/227.15 |
| 5,544,528 A | * | 8/1996 | Woyski et al. ................. 73/665 |
| 5,580,172 A | | 12/1996 | Bhardwaj et al. ........... 374/137 |
| 5,711,603 A | * | 1/1998 | Ringermacher et al. ....... 374/5 |
| 5,789,680 A | | 8/1998 | Fujimoto ..................... 73/719 |
| 5,804,697 A | | 9/1998 | Banaszak .................... 73/1.82 |
| 5,967,660 A | * | 10/1999 | Akpan et al. ................. 374/57 |
| 6,123,455 A | * | 9/2000 | Besheours et al. .......... 374/161 |

FOREIGN PATENT DOCUMENTS

| | | | | |
|---|---|---|---|---|
| EP | 1006346 A1 | * | 12/1998 | |
| GB | 2164147 A | * | 3/1986 | |
| JP | 0154635 | * | 9/1983 | |
| JP | 0085438 | * | 4/1988 | |
| JP | 405172772 A | * | 7/1993 | |
| SU | 1151877 | * | 4/1985 | ................ 374/5 |

OTHER PUBLICATIONS

Thermal and Infrared Nondestructive Testing of Composites and Ceramics. D. Green. Materials Evaluation, vol. 29, No. 11, Nov. 1997.*

* cited by examiner

Primary Examiner—Diego Gutierrez
Assistant Examiner—Gail Verbitsky
(74) Attorney, Agent, or Firm—Gina S. Tollefson; Gerald B. Hollins; Thomas L. Kundert

(57) ABSTRACT

A method and device for visually detecting crack length of a temperature sensitive paint coated test structure during excitation of the test structure. The method and device of the invention capitalizes on surface temperature changes of the test structure as structural fatigue increases. Test structure surface temperature changes are realized in corresponding fluorescence intensity changes in the temperature sensitive paint and recorded with a CCD camera. Improvements over conventional structural fatigue systems include the ability to detect fatigue during flight testing, to record fatigue without stopping the electrodynamic excitation and the ability to detect crack onset and crack length resulting in more accurate cycles-to-fatigue analysis.

16 Claims, 3 Drawing Sheets

METHOD AND DEVICE FOR VISUALLY MEASURING STRUCTURAL FATIGUE USING A TEMPERATURE SENSITIVE COATING

RIGHTS OF THE GOVERNMENT

The invention described herein may be manufactured and used by or for the Government of the United States for all governmental purposes without the payment of any royalty.

BACKGROUND OF THE INVENTION

The field of the invention relates to structural fatigue detection and more particularly to detecting crack length of a structure during out-of-plane excitation by a shaker.

The U.S. Air Force, other government agencies and the automotive industry are interested in high cycle structural fatigue materials to support aircraft and vehicle sustainment and payload capability. High-cycle fatigue is a critical requirement in the development of new materials and structures for airframe and automotive components that will operate under extreme conditions. High-cycle fatigue testing is accomplished by exposing the material or structure to a preselected or known number of vibration cycles and then detecting the corresponding fatigue by determining the onset of a crack. The exposure to vibration cycles is intended to closely simulate an operational environment.

Currently, an electrodynamic shaker employing out-of-plane excitation is used to fatigue aircraft or automotive materials and structures. Out-of-plane excitation refers to exciting a structure perpendicular to the surface area of the structure. During such fatigue testing, the occurrence of a crack is the only criterion for the generation of stress-versus-cycles-to-failure curves for various structural materials. That is, current fatigue testing techniques do not include the capability to detect the length or degree of a crack or failure—merely the existence of a crack or failure. Research in the field of fatigue testing includes investigating methods of determining crack length versus cycles that are similar to the techniques used for in-plane tension/compression fatigue tests. For example, test plates are fatigued using in-plane excitation to generate cracks and traducers and recorders are used to count test cycles.

Problems with known fatigue detection methods include: the inability to detect the onset of a crack during normal operation of the structure, detected cracks grow very rapidly; the vibration of the structure does not allow test personnel to view the crack length versus time or test cycles; the crack is usually extremely thin. These problems make detecting the cracks using conventional video capture techniques extremely difficult. To overcome these limitations, test personnel must stop the excitation (shaker) in order for the crack length to be measured. This can seriously impact the crack-size-versus-cycle curve since the input force must be increased and decreased, meaning that the force input is not kept constant. Techniques for tension/compression crack-size determination require use of gages and clamps which can also affect the dynamic response of the structure under test. Also, attached gages may not survive the vibration test.

The U.S. Air Force is currently attempting to increase the structural life of aging aircraft by applying durability patches after initiation of a crack. Durability patches are made of structural adhesive, viscoelastic material and fiberglass or composite repair material and operate by reducing stress levels at crack tips. Increased knowledge of crack initiation and growth will help verify the utility of such durability patches. Additionally, the ability to determine where a crack will likely form prior to failure will allow preventative maintenance to supplant catastrophic failure.

One significant aspect of structural failures is that a substantial change in the surface temperature occurs as dynamic-fatigue increase. Heretofore, this significant aspect of structural failures has not been successfully employed in detecting cracks or crack length. One possible prior art method of detecting cracks and measuring crack lengths involves the use of a thermography system based on an infrared camera. Drawbacks to this technique include the substantial cost of such systems (well over $200,000 for adequate range and sensitivity) and the large background signal due to ambient heat sources.

There is currently no known valid and accurate way to visually measure crack onset and crack length of a structure during in-laboratory investigation or during a flight test. An accurate, reliable technique to determine crack growth rates is needed in the art. The method and device of the invention provides a technique to accomplish accurate crack onset and growth measurement in structures in an inexpensive, accurate, and non-contacting manner.

SUMMARY OF THE INVENTION

The present invention provides a method and device for visually detecting crack onset and length of a temperature sensitive paint coated test structure during electrodynamic excitation or during flight testing. The method and device of the invention capitalizes on the increased surface temperature changes of the test structure as structural fatigue increases. Test structure surface temperature changes manifest as fluorescence intensity changes in the temperature sensitive paint and are video recorded. Improvements over conventional structural fatigue systems include the ability to record fatigue prior to crack formation, the ability to detect crack length and the ability to detect fatigue during flight testing.

It is therefore an object of the invention to measure crack length while vibrating a structure on an electrodynamic shaker.

It is another object of the invention to measure crack onset while flight testing a structure.

It is another object of the invention to measure crack length of a structure without making contact with the structure.

It is another object of the invention to measure fatigue of a structure being tested on an electrodynamic shaker without stopping the structural exciter.

It is another object of the invention to measure the crack length on a structure being tested relative to the number of excitation cycles applied to the structure.

It is another object of the invention to determine structural crack formation earlier in the failure cycle sequence than conventional methods.

These and other objects of the invention are described in the description, claims and accompanying drawings and are achieved by a structural fatigue investigating visual crack length measurement device comprising:

a test structure coating and test structure fatiguing temperature and intensity responsive temperature sensitive paint;

a test structure excitation signal generator;

a test structure excitation signal recorder; and a thermal sensitivity variation, temperature sensitive paint coated test structure viewing video system, video recorded variations in said temperature sensitive paint corresponding to test structure fatigue.

DETAILED DESCRIPTION

The operation of the device and method of the invention is based on the changing thermal properties of an excited mechanical structure as it fatigues. The more stress and fatigue endured by a test structure, the more the local temperature of the test structure increases. Basing fatigue detection on the local temperature of the test structure allows fatigue or crack onset to be detected and the degree of failure or crack length to be measured. Temperature sensitive paint applied to the test structure changes fluorescent intensity in reaction to the changing surface temperature of the test structure. The changing fluorescent intensity of the temperature sensitive paint of the test structures is visually recorded and analyzed.

Figure 1:
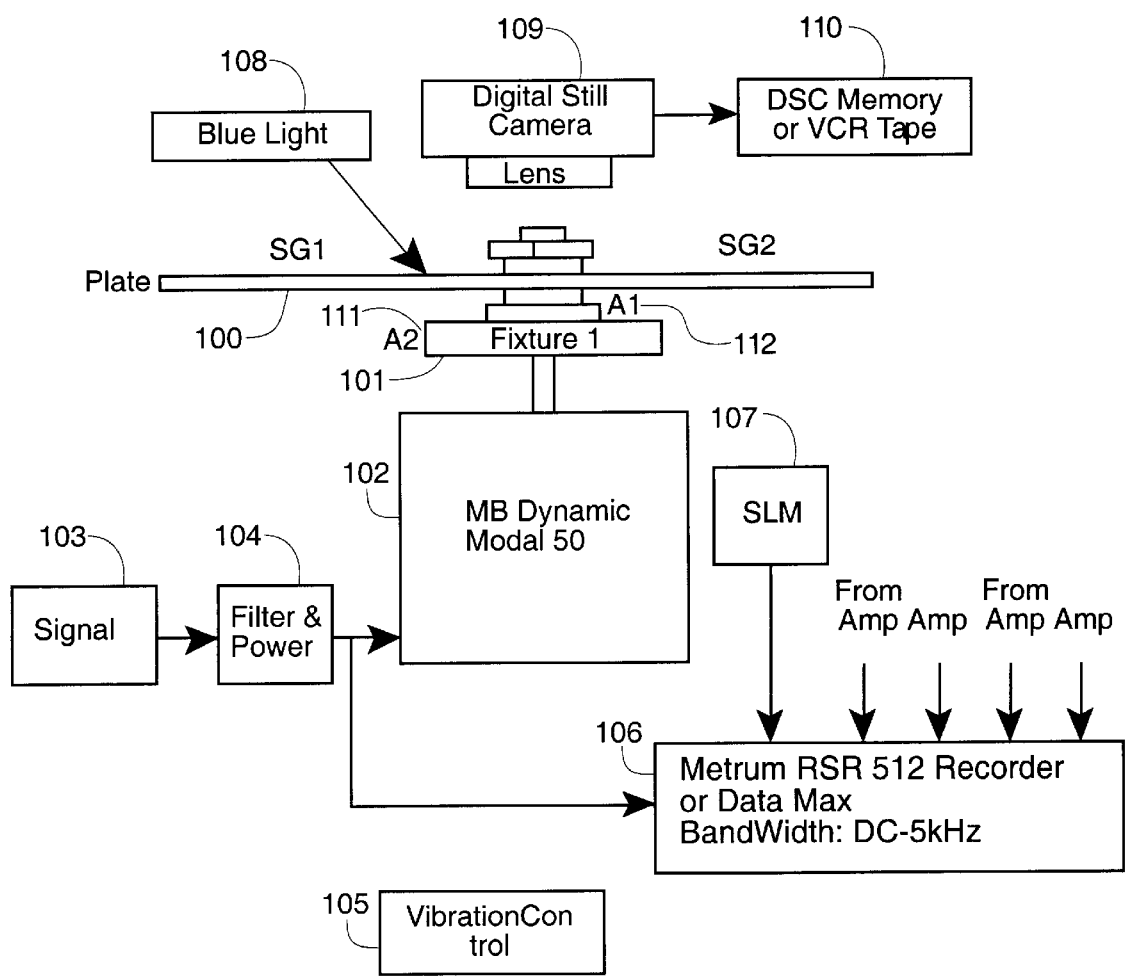
FIG. 1 shows a visual crack measuring system using temperature sensitive coating according to the invention.

FIG. 1 shows a visual crack measurement system using temperature sensitive coating according to the invention. The structure to be fatigued and tested, an aluminum plate, is shown at 100, an electrodynamic shaker 102 is used to fatigue the plate 100 with an interfacing fixture shown at 101. The electrodynamic shaker includes a field coil, an armature, and a mechanical interface to the test structure. Activating the electrodynamic shaker 102 is a signal generator 103. A signal is generated and first transmitted to a signal filter and power amplifier, both represented at 104. The amplified and filtered sinusoidal signal from generator 103 transmits a signal to the electrodynamic shaker 102 and also to a recorder 106 for recording the time history of the structural dynamics signal to help determine the frequency of excitation of the test structure. The plate 100 is coated with a white spray paint primer followed by a temperature sensitive coating. The system shown in FIG. 1 is only one possible arrangement of the invention. Alternative excitation sources, temperature-sensitive coatings and image equipment suitable to accomplish the objects of the invention may also be employed.

The three major image acquisition components include a blue light source represented at 108 for illuminating the temperature sensitive paint coated test structure, a CCD (charged coupled device) camera system represented at 109, and image processing software represented at 110 and used to merge the CCD images and dynamic software components. In the arrangement of FIG. 1, the recording components 106, 109 and 110 are separated, but an alternative arrangement could include all recording components merged into a single computer based measurement system. The CCD camera system 109 is sensitive to the different fluorescent intensity levels in the test structure covered with the temperature sensitive coating. In the arrangement of FIG. 1, the fluorescent intensity level of the CCD camera system 109 is proportional to the temperature differences as the structure starts to crack. The fluorescent intensity level of the CCD camera system varies depending on the structure and chemistry of the selected temperature sensitive paint. The camera 109 and computer 110 capture images of the vibrating test structure 100 during sinusoidal excitation. The electrodynamic shaker 102 excites the structure at resonance to amplify the stress in the test structure 100 to increase the rate of fatigue crack generation of the test structure 100. Excitation of the test structure is not limited to resonance; narrowband random excitation can also be used. During a test, for example, an engineer operates the test system to keep the test structure 100 at resonance. The information thus acquired is used to generate a crack length versus cycles graph. A vibration control system represented by block 105 may be used for more refined shaker signal generation. Appropriate computer software is written and used to merge the crack length versus time obtained from the CCD digital still camera images with the test cycles versus time obtained from the instrumentation data.

A significant feature of the invention includes the ability to detect where a structural fatigue crack will form before it actually forms and taking action to prevent a structural failure. Employing the device and method of the invention in a flight testing scenario on aging aircraft can prevent catastrophic aircraft failures. A test structure with high fluorescent intensity indicating high fatigue and pending structural failure is a candidate for preventative maintenance. The test structure can be structurally repaired or reinforced as necessary and the risk of an in-flight structural failure is thus minimized.

Temperature sensitive coating optimization is a significant aspect of the invention. In general, the polymeric support of the coating dictates the thermal and mechanical stability, adherence characteristics, and surface roughness of the coating as well as contributes to the temperature sensitivity. Control of these parameters allows the formation of temperature sensitive paint systems ideally suited for fatigue testing according to the invention. Sol-gel processing has been shown to be a viable method for the creation of optically transparent, inorganic matrices at relatively mild conditions. The stability and porosity of these films can be manipulated by simply changing the sol-gel processing conditions. Typically, the sol-gel film is deposited on top of a white base coat which serves to stabilize the probe-doped active sol-gel layer, improve adherence of the sol-gel layer, and provide a screen layer suitable for uniform deposition of the sol-gel layer.

Figure 5:
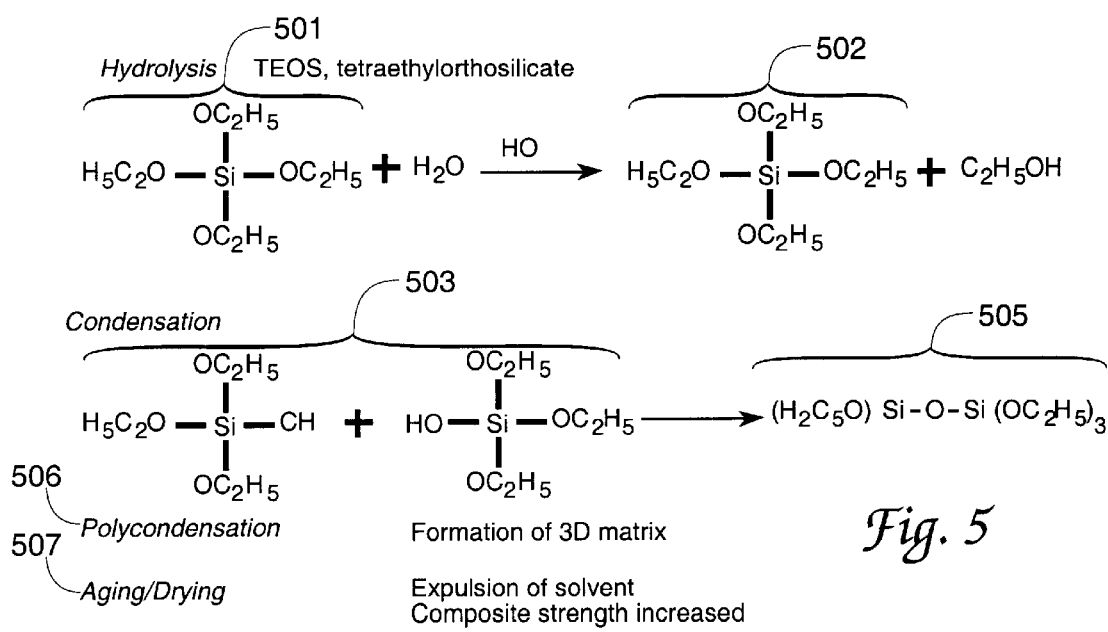
FIG. 5 shows sol-gel processing chemistry.

The sol-gel process allows the formation of controlled-pore glasses under temperature and pressure conditions. Sol-gel processing involves the transition of a solution phase into a gel, followed by densification and loss of solvent. This results in a solid, optically transparent glass. The five-step process as shown in FIG. 5 represents sol-gel chemistry. The process is initiated by the acid- or base-catalyzed hydrolysis of a metal or semi-metal alkoxide such as tetraethylorthosilicate (TEOS) shown at 501 to form the hydrated product shown at 502. Condensation of these moieties shown at 503 results in the formation of metal-oxygen-metal bonds (Si—O—Si) and a colloidal mixture termed a sol shown at 505. Polycondensation of these species, represented at 506, results in the formation of a three-dimensional network and macroscopic solids, as defined by the gelatin point. Subsequent aging and drying of the composite film, represented at 507, caused by the expulsion of solvent from the matrix, increases the composite strength. Host composites for chemical-sensing applications can be easily produced in this manner by incorporating recognition elements (RE, e.g., probe molecules) directly into the sol-gel precursor solution, followed by thin-film deposition. In this manner, the recognition element is entrapped within the porous matrix, and a significant population remains accessible to the external analyte. In addition, the molar ratio of sol-gel precursors, hydrolysis time and temperature, and drying conditions affect the sol-gel processing chemistry and, thus, the physicochemical properties of the final composite (e.g., porosity, polarity). Also, the ambient processing conditions allow the incorporation of luminescent probe species that would otherwise thermally decompose under conventional glass technology.

Several advantages result from the use of sol-gel based composites as binders in the temperature sensitive paint used in the device and method of the invention. First, sol-gel-derived coatings exhibit high thermal stability, making them more capable of withstanding extreme environments than comparable organic binders. Second, a deposition technique that allows the formation of thin, uniform films has recently been developed and has been shown to produce optically transparent, robust composites that possess low surface roughness. Finally, it should be noted that these coatings can be easily removed from most materials by simply destabilizing the base coat with mild solvent, leaving the test surface unaffected.

Figure 6:
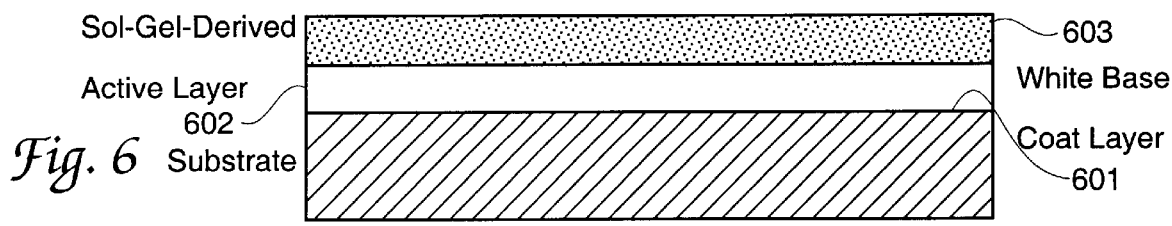
FIG. 6 shows a sol-gel derived temperature sensitive coating.

For adapting this technology to surfaces of various metallic and ceramic substances, the coating architecture illustrated in FIG. 6 was developed. In this approach, a bare surface shown at 601 is cleaned and coated with a white base-coat layer shown at 602. The base coat serves to improve the adherence of the sol-gel layer 603 to the surface, eliminate substrate-induced quenching of the luminescent probe, and mask test-surface irregularities.

Figure 7:
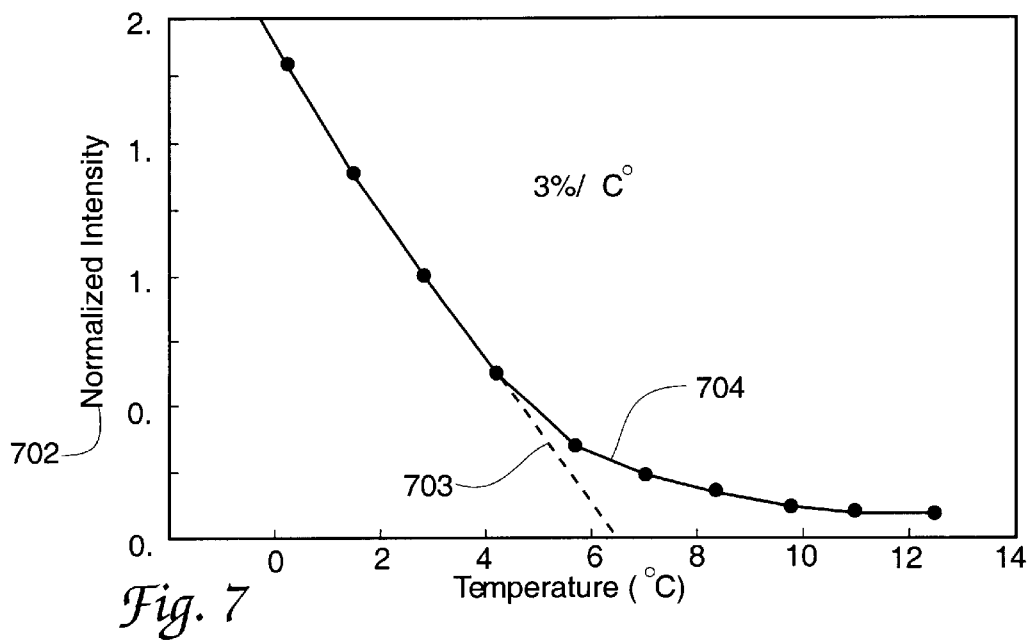
FIG. 7 shows a graph of temperature sensitivity of Pt(TfPP) immobilized in a sol-gel matrix at ambient pressure.

Several molecules have been investigated as possible temperature sensors. One compound for the development of TSPs is platinum esotetra(pentafluorophenyl)porphine [Pt(TfPP)], which has been used in various matrices as a PSP. The temperature sensitivity of Pt(TfPP) in a sol-gel matrix is shown in FIG. 7. In FIG. 7, normalized intensity is shown on the x-axis and temperature is shown on the y-axis. FIG. 7 shows that Pt(TfPP)-based temperature sensitive coatings allow the investigation of materials up to about 60° C.

To validate the use of temperature sensitive paints as a method for investigating dynamic fatigue of materials according to the invention, an aluminum plate is coated with a white base coat followed by a Pt(TfPP)-based sol-gel temperature sensitive paint. For the experiment, the intensity level of the temperature sensitive paint is proportional to temperature differences as the structure starts to crack. Referring again to FIG. 1, the coated aluminum test plate 100 is placed on an electrodynamic shaker 102 and excited continuously at resonant frequency. The excitation frequency is recorded on tape at 106 for determination of cycles versus time. Two accelerometers A1 and A2 shown at 112 and 111, respectively, measuring motion in the plane of excitation and out of the plane of excitation are used to measure the amplitude of the excitation frequency experienced by the plate 100.

Figure 2:
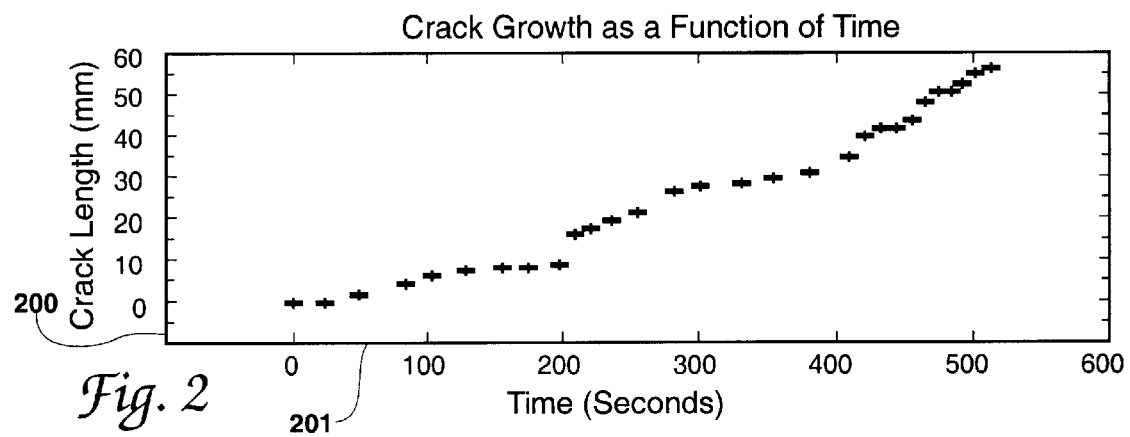
FIG. 2 shows a representative graph of crack length versus time from the video system of the visual crack measuring system of FIG. 1.
Figure 3:
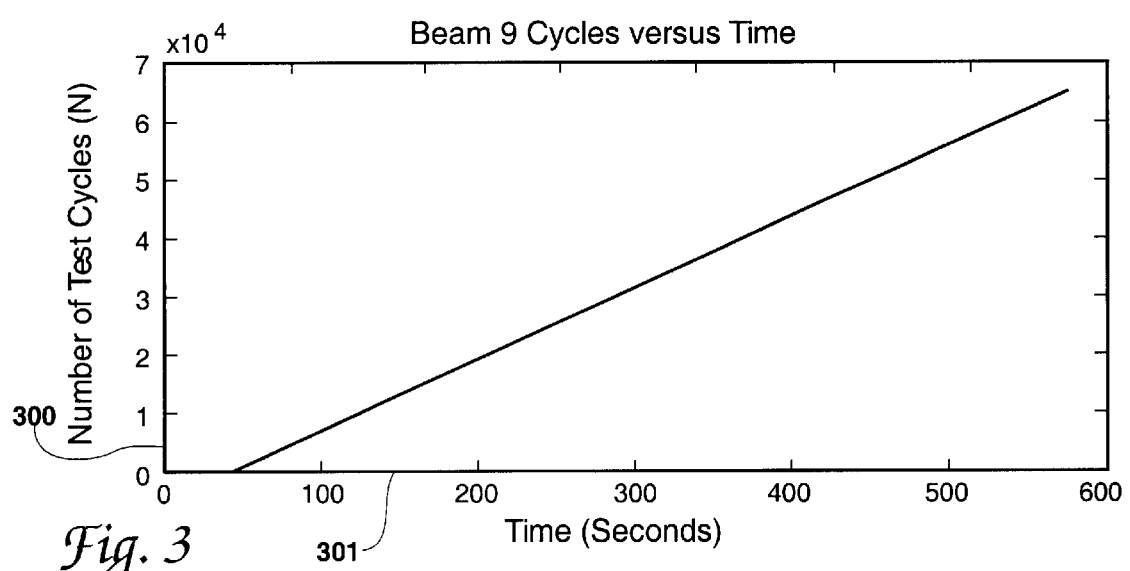
FIG. 3 shows a representative graph of test cycles versus time from the excitation input of the visual crack measuring system of FIG. 1.

To excite the temperature sensitive paint, blue light-emitting-diode arrays, represented at 108 in FIG. 1, are placed above the electrodynamic shaker to illuminate as much of the surface as possible. A CCD camera 109 is placed directly above the plate for image acquisition. Image acquisition begins when the out-of-plane excitation frequency is applied to the aluminum plate 100. Images are acquired by the camera 109 every 2–60 seconds depending on the estimated time required for the crack to initiate and grow to the edge of the plate. FIG. 2 shows crack length versus test time curve generated from 52 CCD images. Crack length is represented on the x-axis at 200 and time is represented on the y-axis at 201. FIG. 3 shows the test cycles versus time curve generated from the instrumentation dynamics data using Matlab software on a PC. Number of test cycles is shown on the x-axis at 300 and time is shown on the y-axis at 301.

Figure 4:
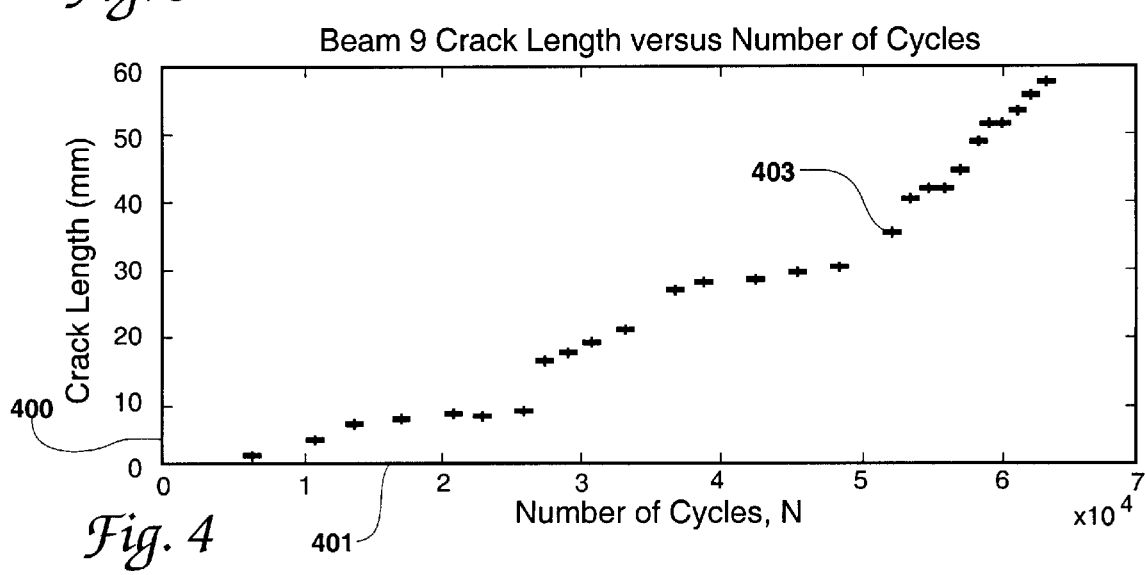
FIG. 4 shows a graph of crack length versus test cycles from the visual crack measuring system of FIG. 1.

Analysis of the images acquired by the camera 109 in FIG. 1 is accomplished by dividing the amplitude of each pixel in an image by the amplitude of each pixel in an initial image before the excitation frequency is applied. This serves as a measure of the intensity change resulting from the vibration of the aluminum plate 100. In the arrangement of FIG. 1, 52 images were collected during an initial test and the crack length as a function of the number of excitation cycles was calculated and the results are show in FIG. 4. FIG. 4 shows the final crack length versus test cycles curves needed by structural design engineers. Crack length is shown on the x-axis at 400 and number of cycles is shown on the y-axis at 401. For the experiment, the visual experiment's end-to-end crack length of 57 millimeters correlates well with the measured length of the crack with a ruler after completion of the vibration test. Discontinuities in the data as at 403 are due to manual tracking of the resonant-frequency and should be smoother with automatic tracking. It should be noted that the invention may be operated using only one LED array for illumination as shown in FIG. 1.

Comparing the method and device of the invention for detecting and measuring cracks with a commercially available thermography system shows the invention as a more effective method of determining cracks. The advantages of using a conventional thermography system are that images can be collected at an accelerated rate (approaching real time) and that the data are already cast as temperature. However, the expense of such systems (typically $200,000 or more) and the large background signal due to ambient heat sources are major disadvantages. Furthermore, thermography system cameras are not sensitive to the visible light spectrum; thus, no cracks are readily apparent in the recovered images.

This method and device of the invention demonstrate the potential of temperature-sensitive paints in applications involving testing of structural materials. Current testing methods often involve the use of out-of-plane excitation provided by an electrodynamic shaker. Using these methods, only the appearance of a crack in the surface can be used as the criterion for failure. However, because of the extreme vibration of the sample, real-time detection and measurement of cracks is difficult at best, requiring the test engineer to stop the test to make measurements. This affects the input levels and the meaning of the number of cycles of excitation. The method and device of the invention makes use of the changes in the surface temperature of the test article as dynamic fatigue increases. These changes are readily observable using standard data-reduction techniques, allowing the near-real-time detection and measurement of crack onset and crack length on surfaces.

The method and device of the invention provides improvements over conventional structural fatigue systems include the ability to record fatigue without stopping the electrodynamic excitation for laboratory tested structures; the ability to detect crack onset and crack length; and the ability to test in flight resulting in more accurate cycles-to-fatigue analysis by capitalizing on the increased surface temperature changes of the test structure as structural fatigue increases.

While the apparatus and method herein described constitute a preferred embodiment of the invention, it is to be understood that the invention is not limited to this precise form of apparatus or method and that changes may be made therein without departing from the scope of the invention which is defined in the appended claims.

We claim:

1. A visual structural fatigue crack length measurement device comprising:

a test structure having a temperature responsive paint coating;

a test structure mechanical excitation means for resonance and narrowband random excitation, said resonance and narrowband random excitation increasing a rate of fatigue crack generation in said test structure wherein, said test structure mechanical excitation means comprises: a signal generator, an excitation signal waveform filter and power amplifier connected to said signal generator, an electrodynamic shaker, and a test structure receiving fixture attaching said test structure to said electrodynamic shaker;

a test structure mechanical excitation means signal recorder;

a video system for viewing and acquiring images of thermal sensitivity variations of the temperature responsive paint coating and for measuring the fatigue crack length in the test structure based on said acquired images wherein, the intensity variations in said temperature responsive paint coating correspond to variations in local temperature of said test structure; and wherein, the variations in the local temperature correspond to said test structure fatigue crack.

2. The visual structural fatigue crack length measurement device of claim 1 wherein said test structure mechanical excitation means signal recorder comprises a test structure excitation signal time history recording sensor connected to a signal generator connected filter and a power amplifier.

3. The visual structural fatigue crack length measurement device of claim 1 wherein said thermal sensitivity variations viewing video system comprises:

a blue light;

a CCD; and video processing software.

4. The visual structural fatigue crack length measurement device of claim 1 further comprising a temperature sensitive paint coating receiving and stabilizing white base coat applied to said test structure.

5. The visual structural fatigue crack length measurement device of claim 4 wherein said test structure paint coating further comprises a probe doped active sol-gel temperature sensitive paint.

6. The visual structural fatigue crack length measurement device of claim 4 wherein said test structure paint coating further comprises a luminescent probe containing sol-gel temperature sensitive paint.

7. The visual structural fatigue crack length measurement device of claim 4 wherein said probe doped active sol-gel temperature sensitive paint comprises platinum meso tetra (pentafluorophenyl)porphine.

8. A visual structural fatigue crack length measurement method comprising the steps:

coating a test structure with a fluorescent intensity varying fatigue-responsive temperature sensitive paint coating, generating a test structure excitation signal by using a test structure mechanical excitation means capable of resonance and narrowband random excitation, said resonance and narrowband random excitation increasing a rate of fatigue crack generation in said test structure;

wherein, said test structure mechanical excitation means comprises: a signal generator, an excitation signal waveform filter and power amplifier connected to said signal generator, an electrodynamic shaker, a test structure receiving fixture to said electrodynamic shaker;

applying said test structure excitation signal to said test structure;

applying said test structure excitation signal to said test structure;

acquire images of a fatigue induced test structure crack using a video system for viewing thermal sensitivity variations of the temperature responsive paint coating and measuring the length of the test structure crack based on acquired images wherein, the intensity variations in said temperature responsive paint coating correspond to variations in local temperature of said test structure; and wherein, the variations in the local temperature are corresponding to said test structure fatigue crack.

9. The visual structural fatigue crack length measurement method of claim 8 further including the step of applying a stabilizing coat of white spray paint to said test structure prior to said coating step.

10. The visual structural fatigue crack length measurement method of claim 9 wherein said coating step further includes the step of coating said test structure with a probe doped active sol-gel temperature sensitive paint.

11. The visual structural fatigue crack length measurement method of claim 10 wherein said coating step further includes coating said test structure with an active sol-gel temperature sensitive paint containing a luminescent probe therein.

12. The visual structural fatigue crack length measurement method of claim 11 wherein said coating step further includes coating said test structure with a platinum mesotetra (pentafluorophenyl)porphine coating.

13. The visual structural fatigue crack length measurement method of claim 8 wherein said recording step further includes the steps of:

sensing a waveform filtered and amplified output signal from said generating step and;

recording a time history output from said sensing step.

14. The visual structural fatigue crack length measurement method of claim 8 wherein said generating step further includes the steps of:

generating an electrical signal;

filtering and amplifying said electrical signal; and vibrating a test structure using an electrical signal activating electrodynamic shaker responsive to said filtered and amplified electrical signal.

15. The visual structural fatigue crack length measurement method of claim 8 wherein said recording step further comprises:

measuring test structure motion using test structure mounted first and second accelerometers;

communicating a signal from said test structure mounted accelerometers to a recorder; and recording an output signal incorporating data from said communicating step.

16. The visual structural fatigue crack length measurement method of claim 8 wherein said video recording step further comprises the steps of:

illuminating the test structure using output energy from a blue light-emitting diode; and acquiring an image comprising pixels of said illuminated test structure using a CCD camera; and determining amplitude of pixels obtained in said acquiring step;

analyzing image from said acquiring step by dividing the amplitude of each pixel in an image by an amplitude of each pixel in an initial image acquired before applying said excitation signal to said test structure to determine the test structure intensity change from said vibrating step.

* * * * *